United States Patent
Frey et al.

(10) Patent No.: US 7,670,557 B2
(45) Date of Patent: Mar. 2, 2010

(54) PLANAR SENSOR ARRANGEMENT, SENSOR ARRAY AND METHOD FOR THE PRODUCTION OF A PLANAR-SENSOR ARRANGEMENT

(75) Inventors: Alexander Frey, Munich (DE); Christian Paulus, Weilheim (DE); Meinrad Schienle, Ottobrunn (DE); Roland Thewes, Gröbenzell (DE)

(73) Assignee: Siemens Aktiengesellschaft, Munich (DE)

( * ) Notice: Subject to any disclaimer, the term of this patent is extended or adjusted under 35 U.S.C. 154(b) by 208 days.

(21) Appl. No.: 11/631,380

(22) PCT Filed: Jun. 30, 2005

(86) PCT No.: PCT/DE2005/001163

§ 371 (c)(1),
(2), (4) Date: Dec. 29, 2006

(87) PCT Pub. No.: WO2006/002617

PCT Pub. Date: Jan. 12, 2006

(65) Prior Publication Data

US 2007/0181424 A1    Aug. 9, 2007

(30) Foreign Application Priority Data

Jun. 30, 2004    (DE) .................. 10 2004 031 672

(51) Int. Cl.
*G01N 31/00*    (2006.01)

(52) U.S. Cl. .......................... 422/82; 422/107; 422/108; 435/6; 435/7.1; 435/287.2; 205/777.5; 204/403.01

(58) Field of Classification Search ........................ None
See application file for complete search history.

(56) References Cited

U.S. PATENT DOCUMENTS 6,281,689 B1    8/2001    Chase et al.

(Continued)

FOREIGN PATENT DOCUMENTS

DE    1 029 820    5/1958

(Continued)

OTHER PUBLICATIONS

M.Paeschke et al.: "Voltammetric Multichannel Measurements Using Silicon Fabricated Microelectrode Arrays", Electroanalysis vol. 8, No. 10, 1996, pp. 891-898.

(Continued)

*Primary Examiner*—Yelena G Gakh
*Assistant Examiner*—Robert Xu
(74) *Attorney, Agent, or Firm*—Harness, Dickey & Pierce, P.L.C.

(57)    ABSTRACT

A planar-sensor arrangement is disclosed, which is used to detect particles possibly contained in an analyte. The sensor element includes a substrate, a first planar-sensor electrode and a second planar-sensor electrode which are formed on and/or in the substrate and whereon catcher molecules can be immobilized. The first sensor-electrode and the second sensor-electrode are divided, respectively, into a plurality of planar sensor-electrode partial areas. The sensor electrode partial areas of the first sensor electrode and the sensor electrode partial areas of the second sensor electrode are arranged in an alternating manner in two dimensions on the surface plane of the substrate. The sensor element also includes a wiring structure by which at least one part of the sensor electrode partial areas of the first sensor electrode are electrically coupled together, and by which at least one part of the sensor-electrode partial areas of the second sensor electrode are electrically coupled together.

20 Claims, 9 Drawing Sheets

U.S. PATENT DOCUMENTS

| | | | |
|---|---|---|---|
| 6,793,389 B2 * | 9/2004 | Chavan et al. | 374/179 |
| 2002/0028441 A1 | 3/2002 | Hintsche et al. | |
| 2003/0186263 A1 * | 10/2003 | Frey et al. | 435/6 |
| 2004/0045839 A1 | 3/2004 | Thewes et al. | |
| 2005/0194250 A1 | 9/2005 | Frey et al. | |

FOREIGN PATENT DOCUMENTS

| | | |
|---|---|---|
| DE | 196 10 115 A1 | 3/2002 |
| DE | 102 24 567 A1 | 12/2003 |
| EP | 1 445 609 A1 | 8/2004 |
| WO | WO 93/22678 A2 | 11/1993 |
| WO | WO 97/21094 A1 | 6/1997 |
| WO | WO 01/43870 A2 | 6/2001 |
| WO | WO 03/083134 A1 | 10/2003 |
| WO | WO 2004/019024 A1 | 3/2004 |

OTHER PUBLICATIONS

R. Hintsche et al.: "Microbiosensors using electrodes made in Si-technology", Frontiers in Biosensorics I—Fundamental Aspects, 1997, pp. 267-283.

P. van Gerwen et al.: "Nanoscaled Interdigitated Electrode Arrays for Biochemical Sensors", "Transducers", IEEE, Int. Conference on Solid-State Sensors and Actuators, 16.—Jun. 19, 1997, Chicago, pp. 907-910.

C. Krause et al.: "Capacitive Detection of Surfactant Adsorption on Hydrophobized Gold Electrodes", Langmuir, Band 12, No. 25, 1996, pp. 6059-6064.

R. Thewes et al.: "CMOS Sensor Interface Arrays for DNA Detection", Proc. 13$^{th}$ Workshop on Advances in Analog Circuit Design (AACD), Apr. 2004, pp. 65-89.

* cited by examiner

PLANAR SENSOR ARRANGEMENT, SENSOR ARRAY AND METHOD FOR THE PRODUCTION OF A PLANAR-SENSOR ARRANGEMENT

PRIORITY STATEMENT

This application is the national phase under 35 U.S.C. §371 of PCT International Application No. PCT/DE2005/001163 which has an International filing date of Jun. 30, 2005, which designated the United States of America and which claims priority on German Patent Application number 10 2004 031 672.4 filed Jun. 30, 2004, the entire contents of which are hereby incorporated herein by reference.

FIELD

Embodiments of the invention generally relate to a planar sensor arrangement, a sensor array and/or a method for the production of a planar sensor arrangement.

BACKGROUND

Two-pole impedance sensors for biosensor technology are known from the prior art, see e.g. [1] to [8]. Furthermore, two-pole impedance methods have also been proposed for the sensor technology of other chemical substances, e.g. in the context of gas sensor technology.

Reference [9] discloses CMOS sensor interface arrays for DNA detection.

A description is given below referring to FIG. 1A, FIG. 1B, of a sensor arrangement 100 in accordance with the prior art.

Figure 1A:
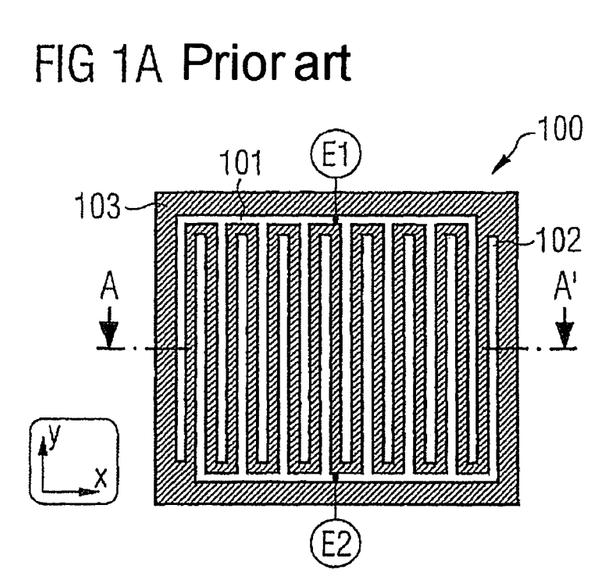
FIGS. 1A and 1B show a plan view and a cross-sectional view of a sensor arrangement including interdigital electrodes in accordance with the prior art.

FIG. 1A shows a plan view of the sensor arrangement 100, which is integrated in a silicon substrate 103. A first interdigital electrode 101 is provided in a first surface region of the silicon substrate 103. A second interdigital electrode 102 is provided in another surface region of the silicon substrate 103. The interdigital electrodes 102, 103 are configured in interdigitated fashion.

Figure 1B:
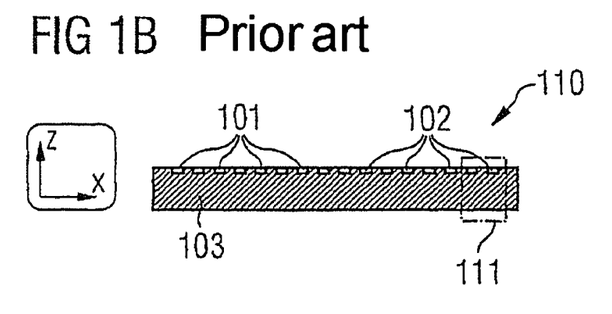

FIG. 1B shows a cross sectional view 110 of the sensor arrangement 100 along a sectional line A-A'.

The sensor arrangement 100 known from [4], [7], [8] can be used for carrying out a two-pole impedance measurement in the context of DNA sensor technology. The sensor electrode 100 contains two interdigital electrodes 101, 102 comprising fingers arranged periodically next to one another in one dimension.

Furthermore, FIG. 1B shows a partial region 110 of the sensor arrangement 100, which partial region is described in more detail below on the basis of FIG. 2A, FIG. 2B in order to elucidate the principle and the functioning of the sensor arrangement 100.

Figure 2A:
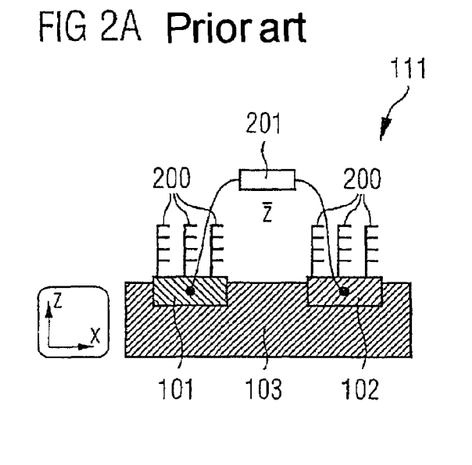
FIGS. 2A, 2B show two operating states of one partial region of the sensor arrangement comprising interdigital electrodes in accordance with the prior art as shown in FIGS. 1A, 1B.

FIG. 2A shows the partial region 111 of the sensor arrangement 100 in a first operating state, in which an analyte having particles to be detected has not been brought into contact with the sensor arrangement 100. Catcher molecules 200, e.g. DNA single strands, are immobilized on the electrodes 101, 102. Gold is often used as material for the interdigital electrodes 101, 102, so that the catcher molecules 200 are immobilized by means of the gold-sulfer coupling—frequently used in biochemistry—between gold material of the interdigital electrodes 101, 102, on the one hand, and thiol groups (SH groups) of the catcher molecules 200 on the other hand.

Figure 2B:
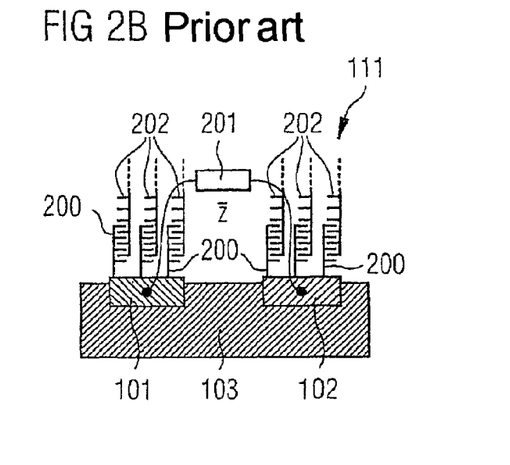

FIG. 2B shows a second operating state of the sensor arrangement 100 after the latter has been brought into contact with an analyte having particles 202 to be detected. Consequently, the analyte to be examined, which comprises an electrolyte possibly having particles 202 to be detected, is situated above the sensor electrodes 101, 102 during active sensor operation. A hybridization, as is illustrated schematically in FIG. 2B, that is to say a bonding of DNA single strands 202 to the catcher molecules 200, takes place only when catcher molecules 200 and DNA single strands 202 match one another in accordance with the key-lock principle, which is referred to as a "match". If this is not the case, then hybridization is not effected. This situation is referred to as a "mismatch". The specificity of the sensor is thus derived from the specificity of the catcher molecules.

The electrical parameter evaluated in accordance with the sensor principle of the sensor in accordance with FIG. 2A, FIG. 2B is the impedance 201 between the electrodes 101, 102, which are shown schematically in FIG. 2A, FIG. 2B. In the case of a hybridization that has taken place (if appropriate after a rinsing step following the hybridization phase), the vale of the impedance 201 changes since DNA molecules 202 and catcher molecules 200 have different electrical properties than the electrolyte, and since electrolyte material is displaced from the region between the electrodes 101, 102 during the hybridization.

Figure 3:
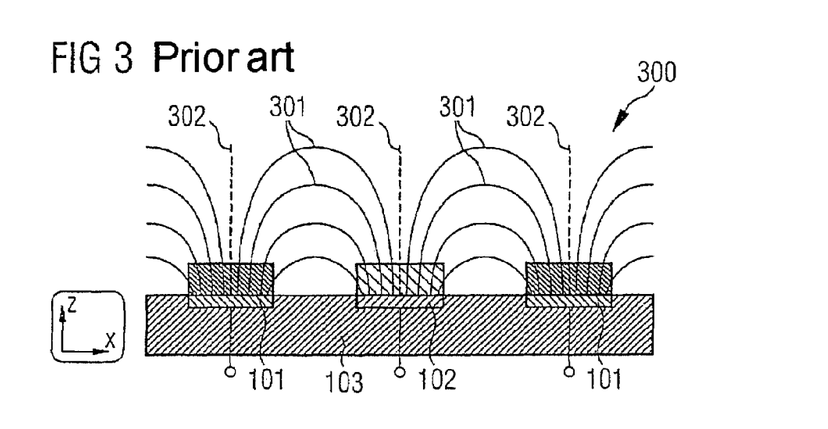
FIG. 3 shows a cross-sectional view of another partial region of the sensor arrangement including interdigital electrodes in accordance with the prior art as shown in FIGS. 1A, 1B.
Figure 4:
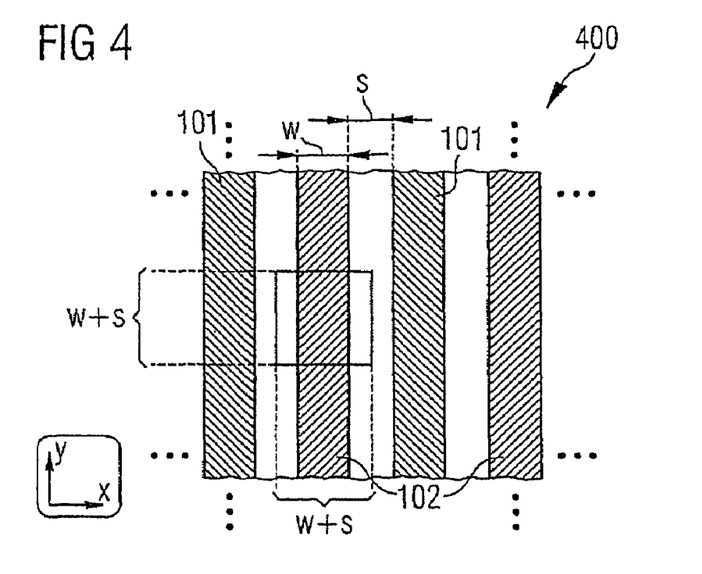
FIG. 4 shows one enlarged partial region of a sensor arrangement including interdigital electrodes in accordance with the prior art.

A description is given below, referring to FIG. 3, of a different partial view 300 of the sensor arrangement 100 from FIG. 1B, in which electrical field lines 301 between the electrodes 101, 102 are depicted schematically. The electrical field line profiles 301 of the interdigital structures 101, 102 have, as shown in FIG. 3, lines of symmetry 302 which can be used for the analytical description and assessment of the properties of the sensor arrangement.

However, the sensor arrangements based on interdigital electrodes known from the prior art, such as the sensor arrangement shown in FIG. 1A to FIG. 3, do not have a sufficient detection sensitivity for many applications.

SUMMARY

In at least one embodiment of the invention, a sensor arrangement is provided, comprising an increased detection sensitivity with respect to an interdigital electrode structure.

In at least one embodiment of the invention, a planar sensor arrangement is provided, by a sensor array and by a method for the production of a planar sensor arrangement.

The planar sensor arrangement according to at least one embodiment of the invention for detecting particles possibly contained in an analyte contains a substrate, a first planar sensor electrode and a second planar sensor electrode which are formed on and/or in the substrate and on which catcher molecules can be immobilized, the first planar sensor electrode and the second sensor electrode in each case being divided into a plurality of planar sensor electrode partial regions, the sensor planar electrode partial regions of the first planar sensor electrode and the sensor electrode partial regions of the second planar sensor electrode being arranged alternately in two dimensions in the surface plane of the substrate. Furthermore, the planar sensor arrangement contains a wiring structure by means of which at least one portion of the sensor electrode partial regions of the first sensor electrode are electrically coupled to one another and by means of which at least one portion of the sensor electrode partial regions of the second sensor electrode are electrically coupled to one another.

Furthermore, at least one embodiment of the invention provides a sensor array comprising a plurality of sensor arrangements comprising the above-described features which are formed on and/or in the substrate.

In the method according to at least one embodiment of the invention for the production of a planar sensor arrangement for detecting particles possibly contained in an analyte, a first planar sensor electrode and a second planar sensor electrode are formed on and/or in a substrate, on which electrodes catcher molecules are immobilized, the first sensor electrode and the second sensor electrode in each case being divided into a plurality of planar sensor electrode partial regions, the sensor electrode partial regions of the second sensor electrode being arranged alternately in two dimensions in the surface plane of the substrate. Furthermore, a wiring structure is formed by means of which at least one portion of the sensor electrode partial regions of the first sensor electrode are electrically coupled to one another and by means of which at least one portion of the sensor electrode partial regions of the second sensor electrode are electrically coupled to one another.

One basic idea of at least one embodiment of the invention can be seen in providing two planar sensor electrodes instead of the interdigital electrode structure known from the prior art, which planar sensor electrodes are in each case formed from a plurality of sensor electrode partial regions that are formed in a surface plane of the substrate and are preferably non-continuous in the plane. The sensor electrode partial regions of the two sensor electrodes are arranged alternately (e.g. in checkered fashion) in two dimensions, namely in two preferably orthogonal directions in the surface plane of the sensor arrangement.

To put it another way, first and second sensor electrode partial regions alternate along a first direction in the surface plane of the substrate, and first and second sensor electrode partial regions alternate along a second direction in the surface plane of the substrate (which preferably runs orthogonally with respect to the first direction). Consequently, at least one sensor electrode partial region of the second sensor electrode is formed in a region surrounding a sensor electrode partial region of the first sensor electrode. As can be shown mathematically (see equations (1) to (42)), such a planar sensor arrangement has a higher detection sensitivity for many scenarios than the interdigital electrode arrangement in accordance with the prior art.

The completely planar surface structure of the sensor arrangement of at least one embodiment of the invention can be manufactured much more simply in terms of process engineering than a three-dimensional electrode structure.

The sensor electrode partial regions of the planar sensor arrangement may be arranged essentially in matrix-type fashion. In accordance with this configuration, the sensor electrode partial regions may be arranged in rows and in columns, thereby clearly resulting in a checkered pattern of first and second sensor electrode partial regions. Apart from sensor electrode partial regions at edge sections of the planar sensor electrodes, in accordance with this configuration one sensor electrode partial region of the first sensor electrode is surrounded by four sensor electrode partial regions of the second sensor electrode as nearest neighbors.

At least one portion of the sensor electrode partial regions in the surface plane of the substrate may have an extent which is less than the distance between the sensor electrode partial region and at least one directly adjacent sensor electrode partial region. As can be shown mathematically (see equations (1) to (42)), in the case of the planar sensor arrangement according to at least one embodiment of the invention, the change in the impedance on account of a sensor event (e.g. a hybridization), in particular the change in the imaginary component of the impedance on account of a sensor event, and hence the detection sensitivity of the planar sensor arrangement can be increased if the extent of the sensor electrode partial regions is chosen to be less than the distance between directly adjacent sensor electrode partial regions.

Catcher molecules may be immobilized on the first planar sensor electrode and/or on the second planar sensor electrode. Such catcher molecules may be, in particular, DNA single strands, proteins, polypeptides or other molecules which can bind arbitrarily with particles to be detected that are contained in an analyte to be investigated (e.g. can hybridize with particles to be detected).

In the case of the planar sensor arrangement of at least one embodiment of the invention, at least one portion of the sensor electrode partial regions in the surface plane of the substrate may have polygonal shape (that is to say the shape of a polygon).

In particular, at least one portion of the sensor electrode partial regions in the surface plane of the substrate may have rectangular or square shape or form.

Furthermore, at least one portion of the sensor electrode partial regions of the planar sensor arrangement in the surface plane of the substrate may have triangular shape.

In accordance with the configuration described last, at least one portion of the sensor electrode partial regions in the surface plane of the substrate may have the shape of equilateral triangles, the triangle sides of adjacent sensor electrode partial regions being arranged parallel to one another.

Alternatively or supplementarily, at least one portion of the sensor electrode partial regions in the surface plane of the substrate may have the shape of isosceles triangles.

Alternatively or supplementarily, at least one portion of the sensor electrode partial regions in the surface plane of the substrate may have the shape of right-angled triangles, the triangle sides of adjacent sensor electrode partial regions being arranged parallel to one another.

Furthermore, at least one portion of the sensor electrode partial regions in the surface plane of the substrate may have round or elliptical shape or form.

The wiring structure of the planar sensor arrangement of at least one embodiment of the invention may be formed as a buried electrically conductive structure within the substrate.

At least one additional integrated component (e.g. a field effect transistor) may be formed in the plane in which the wiring structure is formed as a buried electrically conductive structure. Consequently, it is possible to provide an electrically active plane with the wiring structure and additional integrated components as a buried structure below the sensor electrodes, which constitutes a particularly space-saving configuration. This saves valuable substrate area (e.g. silicon substrate or silicon chip) and creates a miniaturized sensor arrangement.

The at least one additional integrated component may be a CMOS component. To put it another way, the planar sensor arrangement may be set up as a CMOS planar sensor arrangement.

The sensor electrode partial regions of the first sensor electrode and of the second sensor electrode may be arranged alternately and in matrix-type fashion in rows and columns, and the wiring structure may be formed along a course direction which forms an angle of essentially 45° with course directions of the rows and columns. This configuration enables a particularly space-saving and effective wiring and electrical driving of the sensor electrode partial regions.

The planar sensor arrangement may be set up as a biosensor arrangement, alternatively also as a chemosensor arrangement.

In particular, the planar sensor arrangement may be set up as an impedance sensor arrangement, that is to say be set up in such a way that an alteration of the impedance between the sensor electrodes on account of a hybridization event is detected metrologically. The detection of the impedance may include, in particular, the detection of the imaginary part of the impedance, so that, clearly, a change in the capacitance between the sensor electrodes is detected.

The planar sensor arrangement of at least one embodiment of the invention may be set up as a monolithically integrated sensor arrangement, that is to say be integrated in particular in a semiconductor substrate. In particular, a silicon wafer or a silicon chip may be used as the substrate.

Furthermore, the planar sensor arrangement of at least one embodiment of the invention may have a circuit device by means of which the first sensor electrode and the second sensor electrode can be driven.

By way of the circuit device, a temporally variable electrical drive signal may be able to be applied to the sensor electrodes and a temporally variable electrically detection signal may be able to be detected by the sensor electrodes.

Furthermore, at least one amplifier element formed on and/or in the substrate only and/or at least one evaluation element formed on and/or in the substrate may be contained in the planar sensor arrangement. These electrical components may be provided in particular as integrated electrical components and serve for the amplification, the evaluation and/or preprocessing of a sensor signal.

The configurations have been described with reference to the planar sensor arrangement of at least one embodiment of the invention. These configurations also apply to the sensor array having planar sensor arrangements. Furthermore, the configurations of the planar sensor arrangement also apply to the method for the production of a planar sensor arrangement.

BRIEF DESCRIPTION OF THE DRAWINGS

Example embodiments of the invention are illustrated in the figures and are explained in more detail below.

In the figures.

Identical or similar components in different figures are provided with identical reference numerals.

The illustrations in the figures are schematic and not to scale.

DETAILED DESCRIPTION OF THE EXAMPLE EMBODIMENTS

A description is given below, referred to FIG. 4 to FIG. 7, of a mathematical description of the sensor principle of an interdigital electrode structure known from the prior art. This mathematical description considers the relative change in the impedance of an interdigital electrode sensor arrangement in accordance with the prior art (such as the sensor arrangement 100) upon detection of a hybridization event.

FIG. 4 again shows a partial region 400 of the sensor arrangement 100 from FIG. 1, in which the electrode fingers of the first interdigital electrode 101 and of the second interdigital electrode 102 that are arranged alternately in the horizontal direction in accordance with FIG. 4 are shown. The breadth (or width) of an electrode is designated by w and the distance between the adjacent electrodes is designated by s. An area excerpt having the (w+s)×(w+s) arranged centrally over a sensor electrode 101, 102 is furthermore considered. For production engineering reasons (primarily dictated by lithography boundary conditions), similar values are often used for s and for w.

Figure 5:
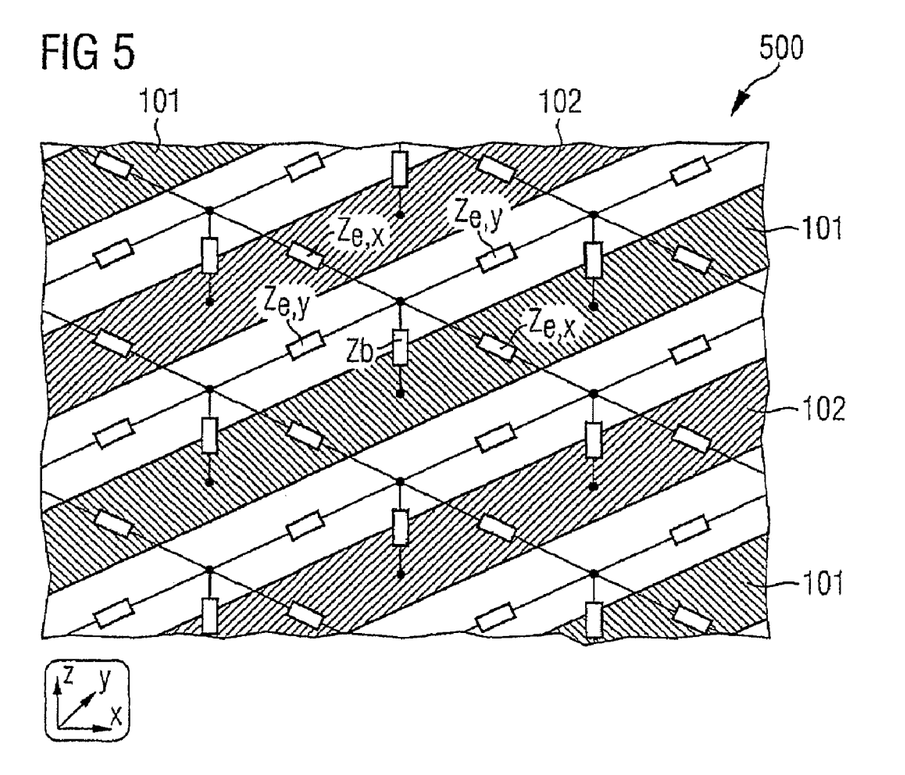
FIG. 5 shows another enlarged partial region of the sensor arrangement including interdigital electrodes in accordance with the prior art.

FIG. 5 again shows a plan view 500 of the sensor arrangement 100. FIG. 5 illustrates an equivalent circuit diagram with concentrated elements. FIG. 5 shows an impedance $Z_b$, the value of which changes on account of a hybridization event, and the electrolyte impedance is $z_{e,x}$ and $z_{e,y}$ in the x direction and in the y direction. Since the potential distribution above the sensor arrangement 100, i.e. in the electrolyte, has no y dependence, at least a good approximation, for symmetry reasons, impedances $Z_{e,y}$ can be disregarded in a further simplification of the equivalent circuit diagram.

Figure 6:
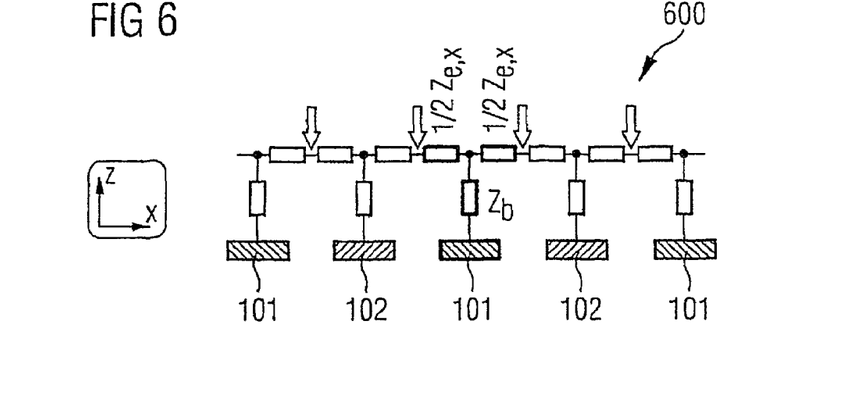
FIG. 6 shows a schematic equivalent circuit diagram of one partial region of a sensor arrangement including interdigital electrodes in accordance with the prior art.

This results in the configuration shown in the equivalent circuit diagram 600 in FIG. 6. It should be noted that all parameters designated by the symbol "Z" in the general representation are complex quantities, that is to say quantities having a real part and having an imaginary part. The components designated by $Z_b$ and $½Z_{e,x}$ in FIG. 6 are associated with a sensor electrode (with an assigned finger of the first interdigital electrode 101 in FIG. 6). The prefactor ½ in the case of the electrolyte resistances results from the fact that this resistance component is assigned respectively half each to the two electrodes 101, 102 above which it is situated in FIG. 5.

Since the values of the impedance $Z_b$ and $½Z_{e,x}$ depend on the choice of the parameters w and s, what is introduced as a standard quantity is the impedance $Z_{b,0}$ which has the (hybridization-dependent) value of the impedance of an electrode 101, 102 of the area (w+s)×(w+s), and the square impedance of the electrolyte $Z_{e,sqr}$. This results in $$Z_b = Z_{b,0} \times [(w+s)^2/((w+s) \times w)] \tag{1}$$

$$\tfrac{1}{2} Z_{e,x} = Ze, \text{sqr} \times [\tfrac{1}{2}(w+s)/(w+s)] \tag{2}$$

and, consequently, for the value of the impedance $Z_{sens}$ associated with an electrode 101, 102:

$$Z_{sens} = Z_{b,0} \times [(w+s)^2/((w+s) \times w)] + \tfrac{1}{2} Z_{e,sqr} \times [\tfrac{1}{2}(w+s)/(w+s)] \tag{3}$$

$$Z_{sens} = Z_{b,0} \times [1 + s/w] + \tfrac{1}{4} Z_{e,sqr} \tag{4}$$

The prefactor ½ before the second term in equation (3) results from the fact that to a good approximation the same electrical potential is present at all the nodes identified by an arrow (see FIG. 6), for symmetry reasons, and the nodes can thus be considered as a common node. This corresponds to a parallel connection of the remaining electrolyte resistances in accordance with equation (2).

The approximation effected is mathematically and physically expedient, particularly if the ratio s/w does not assume overly small values. This requirement made of the validity of the approximation is also met in many scenarios, however, by the technological boundary conditions already discussed above (in particular for reasons of lithography, s and w are often chosen to be similar).

In order to measure the impedance, an (e.g. in antiphase) AC voltage is applied to one (or to both) of the electrodes 101, 102, and the AC current signal that results at the electrodes is evaluated. Ideally, the complex impedance $Z_{b,0}$ has only capacitive components. It has resistive components, these to be regarded as parasitic effects. In this case, by means of choosing a sufficiently high frequency, the operating frequency of the sensor arrangement is brought into a range in which the impedance $Z_{b,0}$ is dominated by the capacitive components. The value of the associated capacitance is designated as $C_{b,0}$.

The impedance of the electrolyte is composed of resistive components and capacitive components. The resistive component, which is modelled by way of the parameter $R_{e,sqr}$ hereinafter, dominates at medium frequencies and the capacitive component, modelled by way of $C_{e,sqr}$ hereinafter, dominates at high frequencies.

With the aid of these quantities, for medium frequencies ($\omega = 2\pi f$), the approximate value $Z_{sens}'$ can be specified for the value of the impedance $Z_{sens}$ associated with an electrode:

$$Z_{sens}' = 1/j\omega C_{b,0} \times [1 + s/w] + \tfrac{1}{4} R_{e,sqr} \tag{5}$$

For high frequencies, the value of the impedance $Z_{sens}$ can be approximated by $Z_{sens}''$:

$$Z_{sens}'' = 1/j\omega \times [C_{b,0} \times (1+s/w) + \tfrac{1}{4} \times 1/C_{e,sqr}] \tag{6}$$

Depending on what electrical or signal-processing evaluation method is used for the measured value of $Z_{sens}$, the magnitude $|Z_{sens}|$ or, in the case of phase-sensitive evaluation, the imaginary part $\text{Im}(Z_{sens})$ can be considered. With equations (5), (6), the following arise for medium frequencies:

$$|Z_{sens}'| = \sqrt{\left(\frac{1+s/w}{\omega C_{b,0}}\right)^2 + \left(\frac{1}{4} \times R_{e,sqr}\right)^2} \tag{7}$$

$$\text{Im}(Z_{sens}') = 1/\omega C_{b,0} \times \{1 + s/w\} \tag{8}$$

For high frequencies, the magnitude and imaginary part are identical, that is to say that the following are obtained:

$$|Z_{sens}''| = 1/\omega \times [1/C_{b,0} \times (1+s/w) + \tfrac{1}{4} \times 1/C_{e,sqr}] \tag{9}$$

$$\text{Im}(Z_{sens}'') = 1/\omega \times [C_{b,0} \times (1+s/w) + \tfrac{1}{4} \times 1/C_{e,sqr}] \tag{10}$$

In order to assess the sensitivity of the sensor comprising interdigital electrodes in accordance with the prior art, the derivative of the magnitude or the imaginary part of the impedance with respect to the magnitude of $Z_{b,0}$ is considered in a manner normalized to the magnitude or the imaginary part of the impedance, which is defined as relative sensitivity $\eta_{abs}$ or $\eta_{im}$:

$$\eta_{abs} = \frac{\partial |Z_{sens}|/\partial |Z_{b,0}|}{|Z_{sens}|} \tag{11}$$

or $$\eta_{im} = \frac{\partial \text{Im}(Z_{sens})/\partial |Z_{b,0}|}{\text{Im}(Z_{sens})} \tag{12}$$

For the sensor arrangement comprising interdigital electrodes in accordance with FIG. 1A to FIG. 5, the following arise for medium frequencies $$\eta_{abs,1'} = \frac{\partial |Z_{sens}|/\partial |Z_{b,0}|}{|Z_{sens}|}$$

$$= \frac{\partial \left(\sqrt{\left(\frac{1+s/w}{\omega C_{b,0}}\right)^2 + \left(\frac{1}{4} \times R_{e,sqr}\right)^2}\right) / \partial \left(\frac{1}{\omega C_{b,0}}\right)}{\sqrt{\left(\frac{1+s/w}{\omega C_{b,0}}\right)^2 + \left(\frac{1}{4} \times R_{e,sqr}\right)^2}} \tag{13}$$

$$\eta_{abs,1'} = \frac{\omega C_{b,0}}{1 + \left(\frac{1}{4} \times \frac{1}{1+s/w} \times \omega C_{b,0} R_{e,sqr}\right)^2} \tag{14}$$

and $$\eta_{im,1'} = \frac{\frac{\partial \text{Im}(Z_{sens})}{\partial |Z_{b,0}|}}{\text{Im}(Z_{sens})} = \frac{\partial \left(\frac{1+s/w}{\omega C_{b,0}}\right) / \partial \left(\frac{1}{\omega C_{b,0}}\right)}{\left(\frac{1+s/w}{\omega C_{b,0}}\right)} \tag{15}$$

$$\eta_{im,1'} = \omega C_{b,0} \tag{16}$$

For high frequencies, the following are obtained:

$$\eta_{abs,1''} = \frac{\partial |Z_{sens}|/\partial |Z_{b,0}|}{|Z_{sens}|}$$

$$= \frac{\partial \left[\frac{1}{\omega} \times \left(1/C_{b,0} \times \left(1 + \frac{s}{w}\right) + \frac{1}{4} \times 1/C_{e,sqr}\right)\right]/\partial \left(\frac{1}{\omega C_{b,0}}\right)}{\frac{1}{\omega} \times \left(1/C_{b,0} \times \left(1 + \frac{s}{w}\right) + \frac{1}{4} \times 1/C_{e,sqr}\right)} \tag{17}$$

$$\eta_{abs,1''} = \frac{\omega C_{b,0}}{1 + \frac{1}{4} \times \frac{1}{1+s/w} \times \frac{C_{b,0}}{C_{e,sqr}}} \tag{18}$$

and, on account of the identity of equations (9) and (10):

$$\eta_{im,1''} = \frac{\frac{\partial \text{Im}(Z_{sens})}{\partial |Z_{b,0}|}}{\text{Im}(Z_{sens})} = \frac{\omega C_{b,0}}{1 + \frac{1}{4} \times \frac{1}{1+s/w} \times \frac{C_{b,0}}{C_{e,sqr}}} \quad (19)$$

Figure 7:
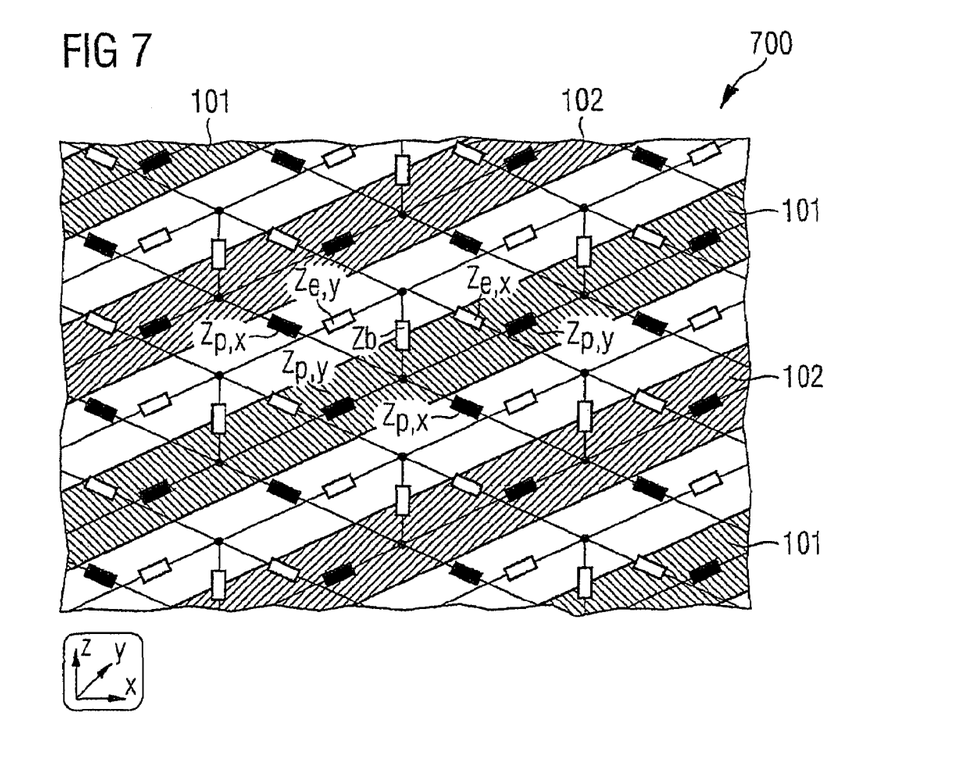
FIG. 7 shows another schematic equivalent circuit diagram of a sensor arrangement including interdigital electrodes in accordance with the prior art.

FIG. 7 shows a different plan view 700 of the sensor arrangement 100, which shows an extended equivalent circuit diagram compared with FIG. 5. In addition to the impedance $Z_b$, the value of which changes on account of a hybridization event, and the electrolyte impedances $Z_{e,x}$ and $Z_{e,y}$ in the x and y directions, FIG. 7 also illustrates the parasitic elements $Z_{p,x}$ and $Z_{p,y}$ in the x and y directions, which represent the impedances which arise directly in the plane of the electrodes 102, 102 and of the carrier material 103 of the sensor electrodes 101, 102. These components can be taken into account computationally in a manner similar to the way this is effected with the aid of equations (1) to (19). However, the computation becomes more complicated as a result and the fundamental statements which are to be made subsequently do not change as a result of this, so that an analytical representation including these impedance components can be dispensed with.

A description is given below, referring to FIG. 8, of a planar sensor arrangement 800 in accordance with a first example embodiment of the invention.

Figure 8:
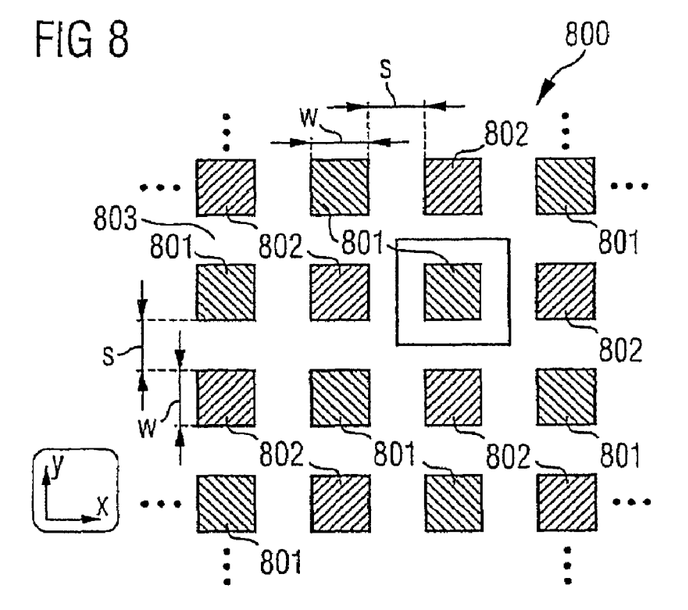
FIG. 8 shows a planar sensor arrangement in accordance with a first example embodiment of the invention.

The planar sensor arrangement 800 shown in FIG. 8 for detecting particles (not shown) possibly contained in an analyte (not shown) contains a silicon substrate 801. Furthermore, the planar sensor arrangement 800 contains a first planar sensor electrode and a second planar sensor electrode which are formed on the silicon substrate 101 and on which catcher molecules (not shown) are immobilized. The first sensor electrode is divided into a plurality of planar first sensor electrode partial regions 801, and the second sensor electrode is divided into a plurality of second planar sensor electrode partial regions 802.

The first sensor electrode partial regions 801 of the first sensor electrode and the second sensor electrode partial regions 802 of the second sensor electrode are arranged alternately in two dimensions in the surface plane of the silicon substrate 803, namely along dimension x and along dimension y in accordance with the paper plane of FIG. 8. Furthermore, a wiring structure (not shown in FIG. 8) is provided in the substrate (below the paper plane of FIG. 8), by which wiring structure the first sensor electrode partial regions 801 are coupled to one another, and by which wiring structure the second sensor electrode partial regions 802 are coupled to one another.

It should be noted that the sensor electrode partial regions 801, 802 are arranged in planar fashion, that is to say are essentially formed in the surface plane of the silicon substrate 803 and do not project, or project only very slightly, from the silicon substrate 803. The surface of the planar sensor electrode partial regions 801, 802 essentially terminates with the surface of the silicon substrate 803.

To put it another way, instead of an arrangement in accordance with FIG. 1 to FIG. 5, a planar sensor arrangement 800 including planar distributed electrode structures is provided according to the invention. In this case, instead of finger electrodes 101, 102, individual areas 801, 802 are used for forming first and second sensor electrodes, which are arranged in a checkered pattern in accordance with FIG. 8. In contrast to the sensor arrangement 100 in accordance with FIG. 1 to FIG. 5, in the case of the planar sensor arrangement 800 an additional wiring plane arranged below the sensor plane is provided in order that the areas 801 associated with one another are electrically connected to one another and in order that the areas 802 associated with one another are connected to one another.

Figure 9:
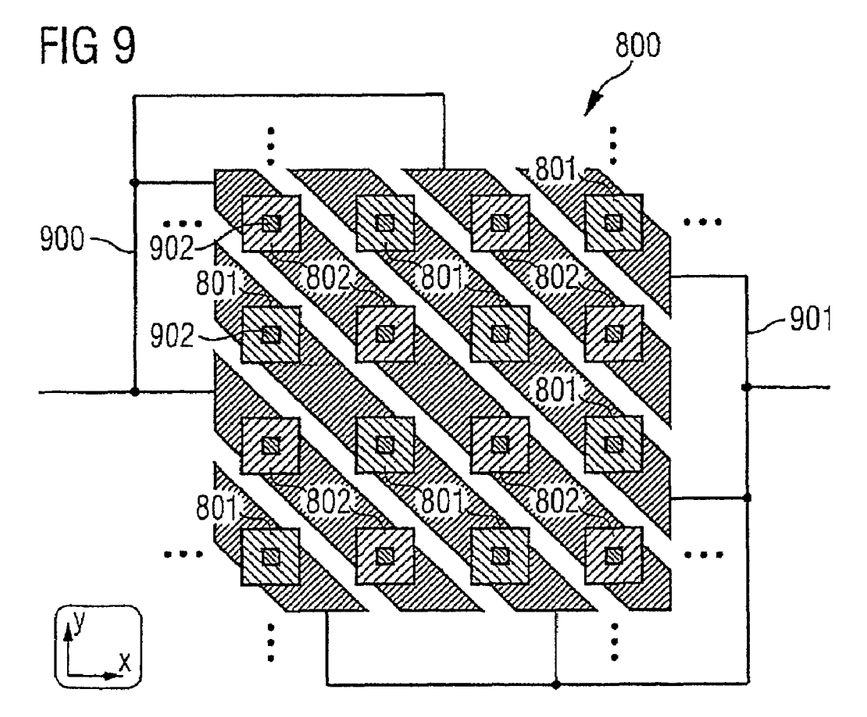
FIG. 9 shows another view of the planar sensor arrangement in accordance with the first example embodiment of the invention.

Such a wiring plane is illustrated in FIG. 9, where the planar sensor arrangement 800 is shown again. The wiring in accordance with FIG. 9 contains a first wiring structure 900, by which the second planar sensor electrode partial regions 802 are electrically coupled to one another. The first planar sensor electrode partial regions 801 are coupled to one another by way of a second wiring structure 901. The first wiring structure 900 and a second wiring structure 901 are electrically decoupled from one another, are realized in a plane below the plane of the first and second planar sensor electrode partial regions 801, 802 and are contact-connected to the sensor electrode partial regions 801, 802 by way of vias 902, i.e. contact-connecting elements oriented perpendicular to the paper plane of FIG. 9.

The first and second sensor electrode partial regions 801, 802 form a matrix-type arrangement, the first and second wiring structures 900, 901 being arranged such that they run at an angle of 45° with respect to the rows and columns of the matrix. The rows and the columns are formed by way of the sensor electrode partial regions 801, 802.

In FIG. 9, the conductor tracks, that is to say the components illustrated as running obliquely, of the first and second wiring structures 900, 901 represent the wiring in the wiring plane lying below the sensor plane, and the vias 902 form the contacts between said plane and the sensor electrodes 801, 802. Since a wiring plane (such as the one in which the first and second wiring structures 900, 901 are formed) is often available in a fabrication process, particularly if the sensor arrangement is fabricated on the basis of a CMOS process, the provision of the wiring plane below the sensor electrode partial regions 801, 802 does not constitute any additional outlay, or constitutes only very small additional outlay.

Figure 10:
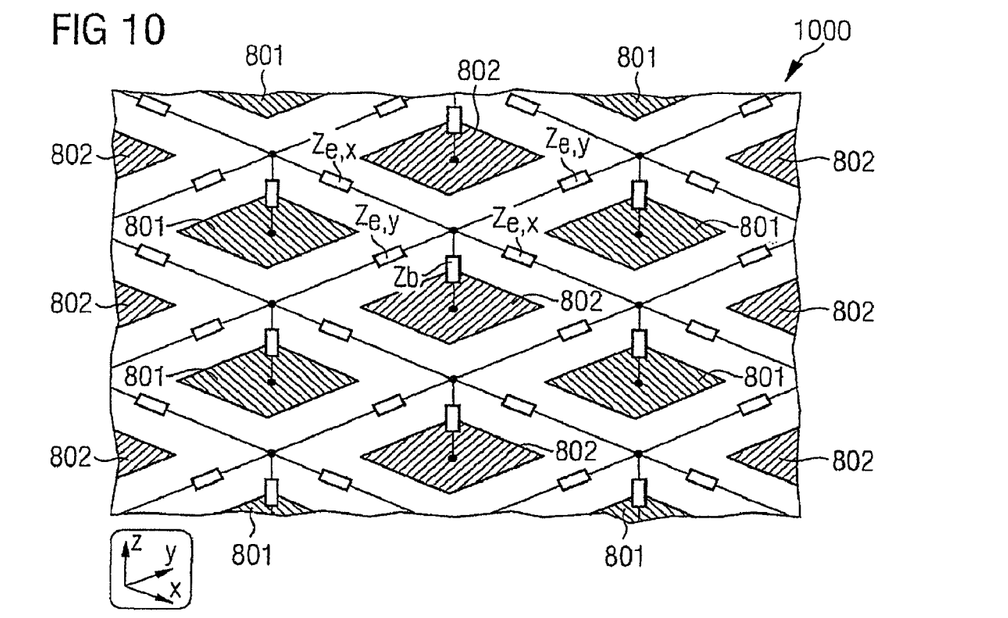
FIG. 10 shows one enlarged partial region of the planar sensor arrangement in accordance with the first example embodiment of the invention.
Figure 11:
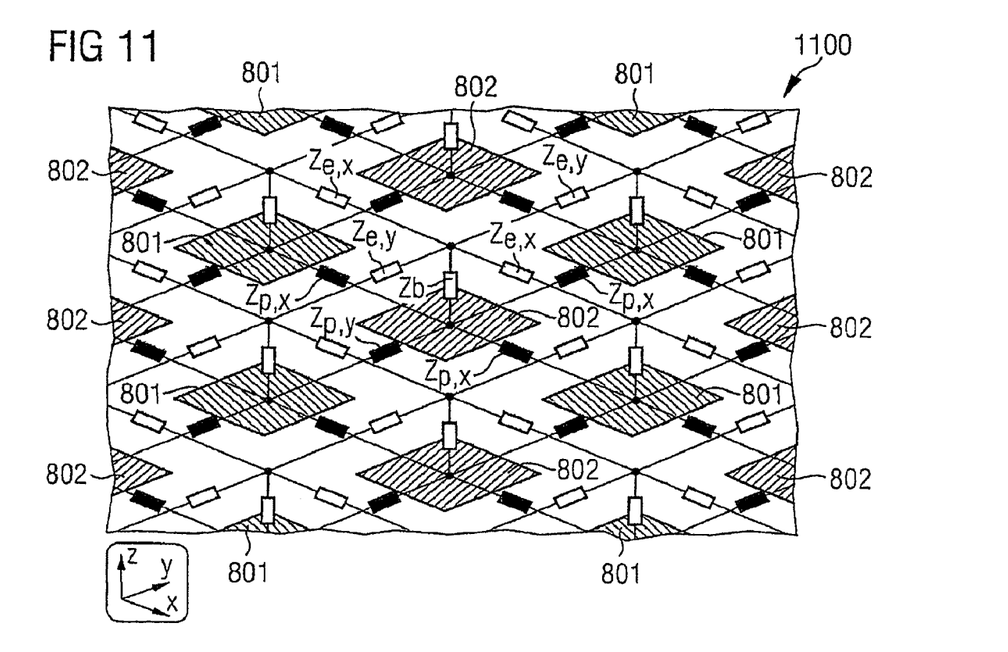
FIG. 11 shows another enlarged partial region of the planar sensor arrangement in accordance with the first example embodiment of the invention.

FIG. 10 shows one plan view 1000 of a partial region of the planar sensor arrangement 800 with a depicted equivalent circuit diagram, similar to that shown in FIG. 5. FIG. 11 shows another plan view 1100 with an analogous extended illustration corresponding to FIG. 7. The elements depicted in FIG. 10, FIG. 11 have the meaning corresponding to that in FIG. 5 and FIG. 7.

In order to calculate the performance of the planar sensor arrangement according to the invention, a calculation corresponding to equations (1) to (19) on the basis of the consideration of FIG. 10 is performed below, whereby a value of the impedance associated with an electrode is obtained:

$$Z_{sens} = Z_{b,0} \times [(w+s)^2/w^2] + \tfrac{1}{4} Z_{e,sqr} \times [\tfrac{1}{2}(w+s)/w] \quad (20)$$

$$Z_{sens} = (1+s/w) \times [Z_{b,0} \times (1+s/w) + \tfrac{1}{8} Z_{e,sqr}] \quad (21)$$

The following arise for medium frequencies:

$$Z_{sens}' = (1+s/w) \times [1/j\omega C_{b,0} \times (1+s/w) + \tfrac{1}{8} R_{e,sqr}] \quad (22)$$

$$|Z_{sens}'| = (1+s/w) \times \sqrt{\left(\frac{1+s/w}{\omega C_{b,0}}\right)^2 + \left(\frac{1}{8} \times R_{e,sqr}\right)^2} \quad (23)$$

$$\text{Im}(Z_{sens}') = 1/\omega C_{b,0} \times (1+s/w)^2 \quad (24)$$

or for high frequencies:

$$Z_{sens}{}''=1/j\omega\times(1+s/w)\times[1/C_{b,0}\times(1+s/w)+\tfrac{1}{8}\times 1/C_{e,sqr}] \quad (25)$$

$$|Z_{sens}{}''|=1/\omega\times(1+s/w)\times[1/C_{b,0}\times(1+s/w)+\tfrac{1}{8}\times 1/C_{e,sqr}] \quad (26)$$

$$Im(Z_{sens}{}'')=1/\omega\times(1+s/w)\times[1/C_{b,0}\times(1+s/w)+\tfrac{1}{8}\times 1/C_{e,sqr}] \quad (27)$$

In order to assess the sensitivity of the planar sensor arrangement 800, the relative sensitivities $\eta_{abs}$ and $\eta_{im}$ are considered again.

The following are obtained for medium frequencies:

$$\eta_{abs,2'} = \frac{\partial |Z_{sens}|/\partial |Z_{b,0}|}{|Z_{sens}|} \quad (28)$$

$$= \frac{\partial\left((1+s/w)\times\sqrt{\left(\frac{1+s/w}{\omega C_{b,0}}\right)^2 + \left(\frac{1}{8}\times R_{e,sqr}\right)^2}\right)/\partial\left(\frac{1}{\omega C_{b,0}}\right)}{\sqrt{(1+s/w)\times\left(\frac{1+s/w}{\omega C_{b,0}}\right)^2 + \left(\frac{1}{8}\times R_{e,sqr}\right)^2}}$$

$$\eta_{abs,2'} = \frac{\omega C_{b,0}}{1+\left(\frac{1}{8}\times\frac{1}{1+s/w}\times\omega C_{b,0}R_{e,sqr}\right)^2} \quad (29)$$

and $$\eta_{im,2'} = \frac{\frac{\partial Im(Z_{sens})}{\partial |Z_{b,0}|}}{Im(Z_{sens})} = \frac{\partial\left(\frac{(1+s/w)^2}{\omega C_{b,0}}\right)/\partial\left(\frac{1}{\omega C_{b,0}}\right)}{\left(\frac{(1+s/w)^2}{\omega C_{b,0}}\right)} \quad (30)$$

$$\eta_{im,2}=\omega C_{b,0} \quad (31)$$

The following are obtained for high frequencies:

$$\eta_{abs,2''} = \frac{\partial |Z_{sens}|/\partial |Z_{b,0}|}{|Z_{sens}|} \quad (32)$$

$$= \frac{\partial\left[\frac{1}{\omega}\times\left(1/C_{b,0}\times\left(1+\frac{s}{w}\right)+\frac{1}{8}\times 1/C_{e,sqr}\right)\right]}{\partial\left(\frac{1}{\omega C_{b,0}}\right)}{\frac{1}{\omega}\times\left(1/C_{b,0}\times\left(1+\frac{s}{w}\right)+\frac{1}{8}\times 1/C_{e,sqr}\right)}$$

$$\eta_{abs,2''} = \frac{\omega C_{b,0}}{1+\frac{1}{8}\times\frac{1}{1+s/w}\times\frac{C_{b,0}}{C_{e,sqr}}} \quad (33)$$

and, on account of the identity of equations (26) and (27)

$$\eta_{im,2''} = \frac{\frac{\partial Im(Z_{sens})}{\partial |Z_{b,0}|}}{Im(Z_{sens})} = \frac{\omega C_{b,0}}{1+\frac{1}{8}\times\frac{1}{1+s/w}\times\frac{C_{b,0}}{C_{e,sqr}}} \quad (34)$$

The sensitivities of the planar sensor arrangement 800 including distributed electrode structures according to an embodiment of the invention and the configuration in accordance with FIG. 1 comprising interdigital electrodes as known from the prior art are related to one another below.

The following are obtained in the assessment of the magnitudes during operation at medium frequencies:

$$\eta_{abs,2'}/\eta_{abs,1'} = \frac{\omega C_{b,0}}{1+\left(\frac{1}{8}\times\frac{1}{1+s/w}\times\omega C_{b,0}R_{e,sqr}\right)^2} \bigg/ \frac{\omega C_{b,0}}{1+\left(\frac{1}{4}\times\frac{1}{1+s/w}\times\omega C_{b,0}R_{e,sqr}\right)^2} \quad (35)$$

$$\eta_{abs,2'}/\eta_{abs,1'} = \frac{1+4\times\left(\frac{1}{8}\times\frac{1}{1+s/w}\times\omega C_{b,0}R_{e,sqr}\right)^2}{1+\left(\frac{1}{8}\times\frac{1}{1+s/w}\times\omega C_{b,0}R_{e,sqr}\right)^2} \quad (36)$$

$$\eta_{abs,2'}/\eta_{abs,1'}>1 \quad (37)$$

The following is obtained upon assessment of the imaginary parts during operation at medium frequencies:

$$\eta_{im,2'}/\eta_{im,1'}=\omega C_{b,0}/\omega C_{b,0}=1 \quad (38)$$

The assessment of the magnitudes and the imaginary part during operation at high frequencies yields:

$$\eta_{abs,2''}/\eta_{abs,1''} = \eta_{im,2''}/\eta_{im,1''} = \quad (39)$$

$$= \frac{\omega C_{b,0}}{1+\frac{1}{8}\times\frac{1}{1+s/w}\times\frac{C_{b,0}}{C_{e,sqr}}} \bigg/ \frac{\omega C_{b,0}}{1+\frac{1}{4}\times\frac{1}{1+s/w}\times\frac{C_{b,0}}{C_{e,sqr}}} \quad (40)$$

$$= \frac{1+2\times\left(\frac{1}{8}\times\frac{1}{1+s/w}\times\frac{C_{b,0}}{C_{e,sqr}}\right)}{1+\left(\frac{1}{8}\times\frac{1}{1+s/w}\times\frac{C_{b,0}}{C_{e,sqr}}\right)} \quad (41)$$

$$\eta_{abs,2''}/\eta_{abs,1''}=\eta_{im,2''}/\eta_{im,1''}>1 \quad (42)$$

It can be seen from equations (37), (38) and (42) that the sensor configuration according to an embodiment of the invention is equivalent or superior to the configurations disclosed in [4], [7], [8] in all relevant operating modes (that is to say, in particular, in all frequency ranges).

It should be noted that the plausibility computation referring to equations (1) to (42) with a simple equivalent circuit diagram corresponds to a profile of the field lines in the electrolyte in the xy plane which run either only in the x direction or only in the y direction.

Figure 12A:
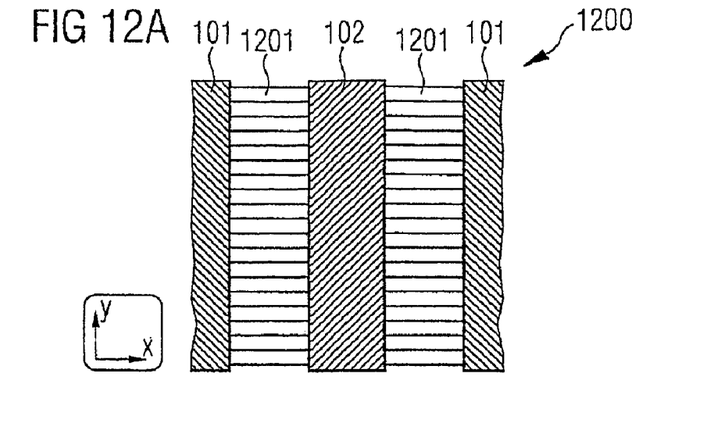
FIGS. 12A to 12C show schematic diagrams with the electric field line profile of an interdigital electrode structure in accordance with the prior art and a planar sensor arrangement according to an embodiment of the invention.
Figure 12B:
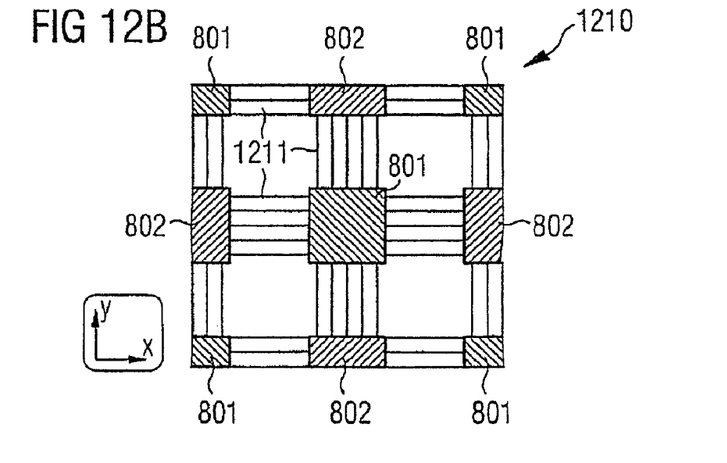
Figure 12C:
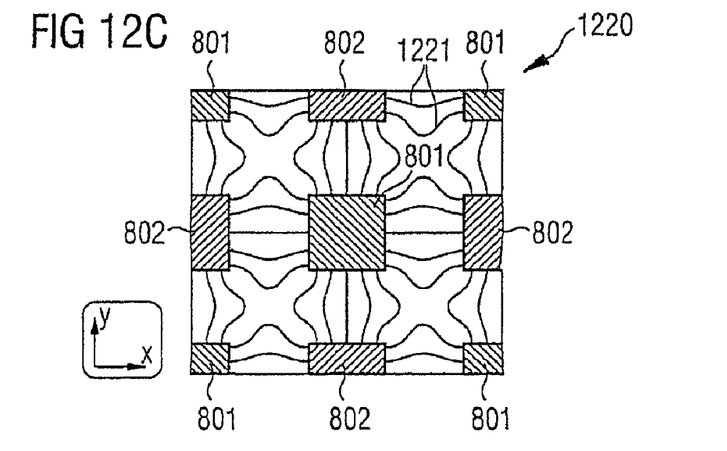

For the sensor arrangement 100, the computation is based on the field line profile 1201 of the partial region 1200 from FIG. 12A. A field line profile 1211 as shown in partial region 1210 in FIG. 12B is assumed for the planar sensor arrangement 800 according to an embodiment of the invention. The assumption in accordance with FIG. 12A is very realistic for the sensor arrangement 100 in accordance with FIG. 1 to FIG. 5 for reasons of symmetry. For the planar sensor arrangement 800 of an embodiment of the invention including distributed electrodes in accordance with FIG. 8, however, a field line profile 1221 such as corresponds to the partial region 1220 shown in FIG. 12C is more realistic than the idealized illustration in FIG. 12B. The effective lengthening of the field lines 1221 shown in FIG. 12C compared with the idealized computationally simpler illustration from FIG. 12B results qualitatively in an increase in the impedance of the electrolyte. Consequently, even greater values for the parameter $\eta$ arise for the planar sensor arrangement 800 from FIG. 8, that is to say that the sensor according to the invention is to some extent even better than is apparent from equations (20) to (42).

Figure 14:
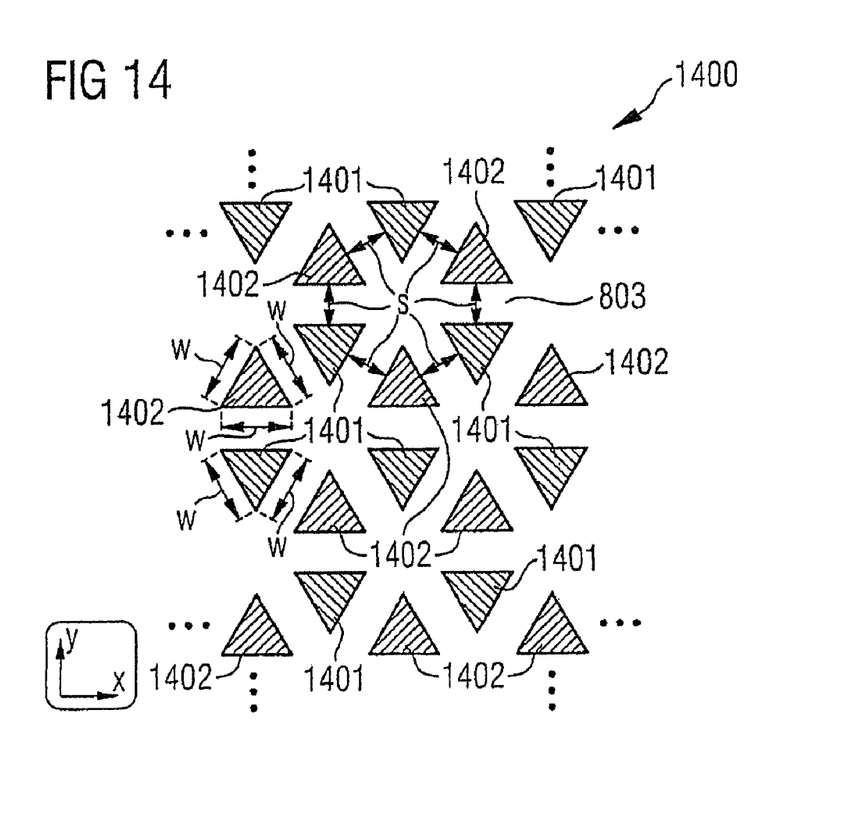
FIG. 14 shows a planar sensor arrangement in accordance with a third example embodiment of the invention.
Figure 15:
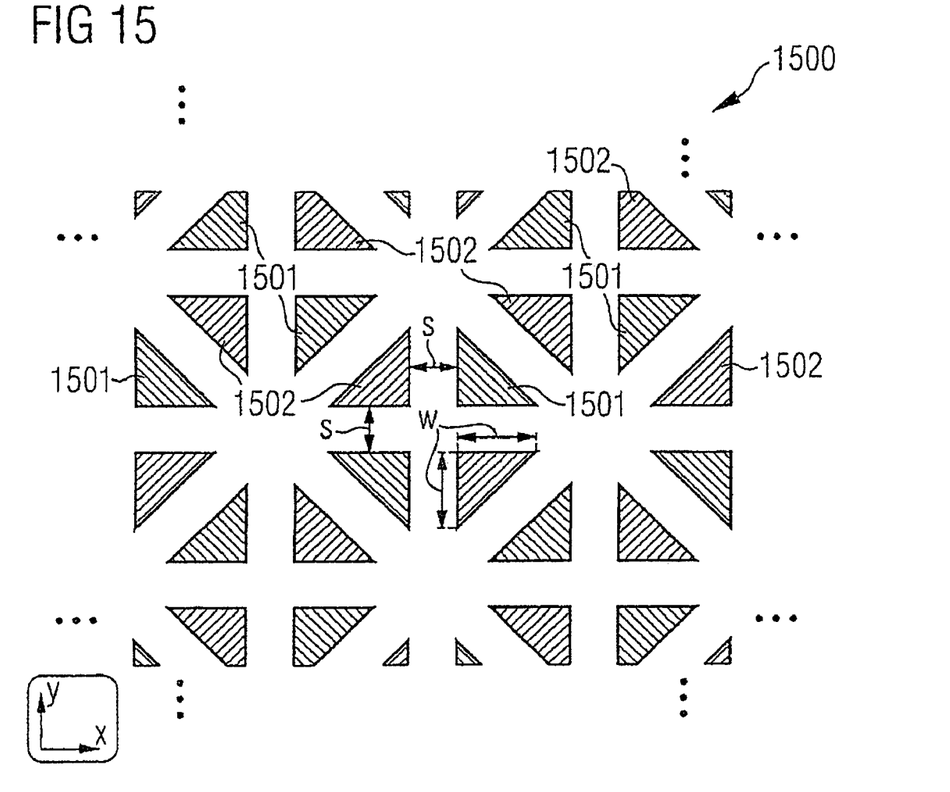
FIG. 15 shows a planar sensor arrangement in accordance with a fourth example embodiment of the invention.

Alternative geometries for the planar sensor electrode partial regions are described below with reference to FIG. 13 to FIG. 15. It should be noted that any other electrode configuration desired is possible and the geometries illustrated in FIG. 8, and FIG. 13 to FIG. 15 are mentioned only by way of example.

Figure 13:
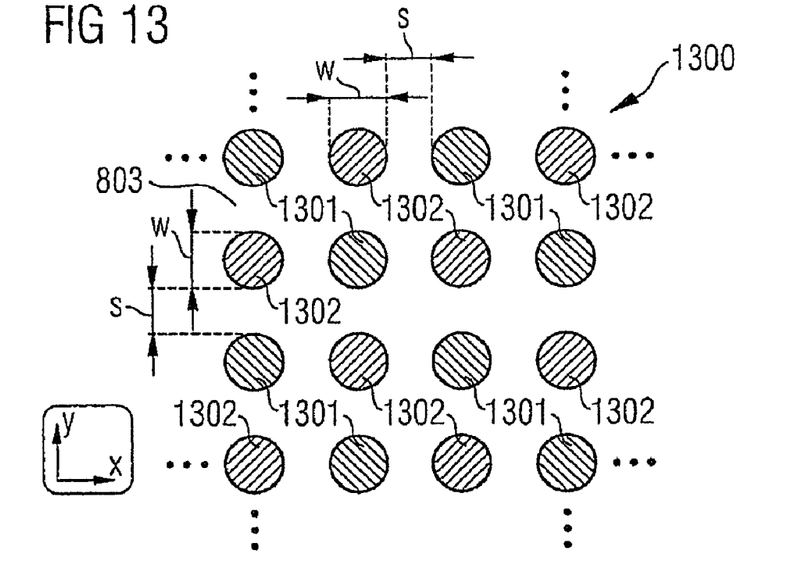
FIG. 13 shows a planar sensor arrangement in accordance with a second example embodiment of the invention.

A planar sensor arrangement 1300 in accordance with a second example embodiment of the invention is described in FIG. 13.

In the case of the planar sensor arrangement 1300, the sensor electrode partial regions of a first sensor electrode that are arranged in checkered fashion are formed by way of first planar round sensor electrode partial regions 1301 and the sensor electrode partial regions of a second sensor electrode 1302 are formed by way of second planar round sensor electrode partial regions 1302.

A description is given below, referring to FIG. 14, of a planar sensor arrangement 1400 in accordance with a third example embodiment of the invention.

In FIG. 14, the first sensor electrode is formed by means of first planar triangular sensor electrode partial regions 1401 and the second sensor electrode is formed by way of second planar triangular sensor electrode partial regions 1402, so that triangle-shaped sensor electrode partial regions are provided. The sensor electrode partial regions 1401, 1402 have the form of equilateral triangles in the surface plane of the silicon substrate 803, the triangle sides of adjacent sensor electrode partial regions being arranged parallel to one another.

A description is given below, referring to FIG. 15, of a planar sensor arrangement 1500 in accordance with a fourth example embodiment of the invention.

In the case of the planar sensor arrangement 1500, the first and second sensor electrodes are in turn realized by way of first planar triangular sensor electrode partial regions 1501 and by way of second planar triangular sensor electrode partial regions 1502. The sensor electrode partial regions 1501, 1502 in the surface plane of the silicon substrate 803 have the shape of right-angled triangles, the triangular sides of adjacent sensor electrode partial regions 1501, 1502 being arranged parallel to one another.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The following publications are cited in this document:

[1] Paeschke, M et al. (1996), Electroanalysis 1996(8), No. 10, pp. 849-964
[2] Hintzsche, R et al. (1997) "Microbiosensors using electrodes made in Si-technology", In: "Frontiers in Biosensorics I—Fundamental Aspects", Scheller, F W et al. (eds.), Birkhauser Verlag Basel
[3] WO 93/22678
[4] DE 196 10 115 A1
[5] Van Gerwen, P et al. (1997) "Transducers" '97", pp. 907-910
[6] Krause, C et al. (1996), Langmuir, Volume 12, No. 25, pp. 6059-6064
[7] WO 01/43870 A2
[8] WO 97/21094
[9] Thewes, R et al. (April 2004) "CMOS Sensor Interface Arrays for DNA Detection", Proc 13th Workshop on Advances in Analog Circuit Design (AACD)

LIST OF REFERENCE SYMBOLS

100 Sensor Arrangement
101 First interdigital electrode
102 Second interdigital electrode
103 Silicon substrate
110 Cross-section view
111 Partial region
200 Catcher molecule
201 Impedance
202 Particles to be detected
300 Partial view
301 Field line profile
302 Lines of symmetry
400 Partial region
500 Plan view
600 Equivalent circuit diagram
700 Plan view
800 Planar sensor arrangement
801 First planar sensor electrode partial regions
802 Second planar sensor electrode partial regions
803 Silicon substrate
900 First wiring structure
901 Second wiring structure
902 Vias
1000 Plan view
1100 Plan view
1200 Partial region
1201 Field line profile
1210 Partial region
1211 Field line profile
1220 Partial region
1221 Field line profile
1300 Planar sensor arrangement
1301 First planar round sensor electrode partial regions
1302 Second planar round sensor electrode partial regions
1400 Planar sensor arrangement
1401 First planar triangular sensor electrode partial regions
1402 Second planar triangular sensor electrode partial regions
1500 Planar sensor arrangement
1501 First planar triangular sensor electrode partial regions
1502 Second planar triangular sensor electrode partial regions

The invention claimed is:

1. A planar impedance sensor arrangement for detecting particles possibly contained in an analyte, comprising:
a substrate;
a first planar sensor electrode configured to immobilize catcher molecules;
a second planar sensor electrode configured to immobilize the catcher molecules, the first and second planar sensor electrodes being formed at least one of on and in the substrate, the first sensor electrode and the second sensor electrode each being divided into a plurality of planar sensor electrode partial regions, the sensor electrode partial regions of the first sensor electrode and the sensor electrode partial regions of the second sensor electrode being arranged alternately in two dimensions in a surface plane of the substrate;
a wiring structure, by which at least one portion of the sensor electrode partial regions of the first sensor electrode are electrically coupled to one another and by which at least one portion of the sensor electrode partial regions of the second sensor electrode are electrically coupled to one another; and an evaluation unit integrated in the substrate, the evaluation unit being configured to evaluate an impedance alteration sensor signal, wherein each of the planar sensor electrode partial regions of the first and second planar sensor electrodes has a width, in the surface plane of the substrate, that is less than a distance between a nearest edge of directly-adjacent planar sensor electrode partial regions.

2. The planar sensor arrangement as claimed in claim 1, wherein the sensor electrode partial regions are arranged essentially in matrix-type fashion.

3. The planar sensor arrangement as claimed in claim 1, wherein at least one portion of the sensor electrode partial regions in the surface plane of the substrate has polygonal shape.

4. The planar sensor arrangement as claimed in claim 3, wherein at least one portion of the sensor electrode partial regions in the surface plane of the substrate has at least one of a rectangular and square shape.

5. The planar sensor arrangement as claimed in claim 3, wherein at least one portion of the sensor electrode partial regions in the surface plane of the substrate has triangular shape.

6. The planar sensor arrangement as claimed in claim 5, wherein at least one portion of the sensor electrode partial regions in the surface plane of the substrate has the shape of equilateral triangles, the triangle sides of adjacent sensor electrode partial regions being arranged parallel to one another.

7. The planar sensor arrangement as claimed in claim 5, wherein at least one portion of the sensor electrode partial regions in the surface plane of the substrate has the shape of right-angled triangles, the triangle sides of adjacent sensor electrode partial regions being arranged parallel to one another.

8. The planar sensor arrangement as claimed in claim 1, wherein at least one portion of the sensor electrode partial regions in the surface plane of the substrate has at least one of a round and elliptical shape.

9. The planar sensor arrangement as claimed in claim 1, wherein the wiring structure is formed as a buried electrically conductive structure within the substrate.

10. The planar sensor arrangement as claimed in claim 9, wherein at least one additional integrated component is formed in a same plane in which the wiring structure is formed as the buried electrically conductive structure.

11. The planar sensor arrangement as claimed in claim 10, wherein the at least one additional integrated component is a CMOS component.

12. The planar sensor arrangement as claimed in claim 1, wherein the sensor electrode partial regions of the first sensor electrode and of the second sensor electrode are arranged alternately in matrix-type fashion in rows and columns, and wherein the wiring structure is formed along a course direction which forms an angle of essentially 45° with course directions of the rows and columns.

13. The planar sensor arrangement as claimed in claim 1, wherein the planar sensor arrangement is set up as a biosensor arrangement.

14. The planar sensor arrangement as claimed in claim 1, wherein the planar sensor arrangement is set up as a monolithically integrated sensor arrangement.

15. The planar sensor arrangement as claimed in claim 1, further comprising a circuit device configured to drive the first sensor electrode and the second sensor electrode.

16. The planar sensor arrangement as claimed in claim 15, wherein the circuit device is configured to apply a temporally variable electrical drive signal to the first and second sensor electrodes, the first and second electrodes being configured to detect a temporally variable electrically detection signal.

17. The planar sensor arrangement as claimed in claim 1, further comprising at least one of
at least one amplifier element formed at least one of on and in the substrate and;
at least one evaluation element formed at least one of on and in the substrate.

18. A sensor array, comprising a plurality of planar sensor arrangements as claimed in claim 1, formed at least one of on and in the substrate.

19. A method for the production of a planar impedance sensor arrangement for detecting particles possibly contained in an analyte, comprising:
forming a first planar sensor electrode and a second planar sensor electrode at least one of on and in a substrate, the first and second sensor electrodes each being capable of immobilizing catcher molecules, the first sensor electrode and the second sensor electrode each being divided into a plurality of planar sensor electrode partial regions, the sensor electrode partial regions of the first sensor electrode and the sensor electrode partial regions of the second sensor electrode being arranged alternately in two dimensions in a surface plane of the substrate;
forming a wiring structure, by which at least one portion of the sensor electrode partial regions of the first sensor electrode are electrically coupled to one another and by which at least one portion of the sensor electrode partial regions of the second sensor electrode are electrically coupled to one another, and
forming an evaluation unit integrated in the substrate, the evaluation unit evaluating an impedance alteration sensor signal,
wherein each of the planar sensor electrode partial regions of the first and second planar sensor electrodes has a width, in the surface plane of the substrate, that is less than a distance between a nearest edge of directly-adjacent planar sensor electrode partial regions.

20. The planar sensor arrangement as claimed in claim 4, wherein at least one portion of the sensor electrode partial regions in the surface plane of the substrate has triangular shape.

* * * * *